US00PP37438P2

(12) United States Plant Patent
Brown

(10) Patent No.: US PP37,438 P2
(45) Date of Patent: May 26, 2026

(54) ***MANDEVILLA* PLANT NAMED 'KLEMS22083'**

(50) Latin Name: *Mandevilla sanderi*
Varietal Denomination: KLEMS22083

(71) Applicant: KLEMM + SOHN GMBH & CO. KG, Stuttgart (DE)

(72) Inventor: Graham N. Brown, Bowral (AU)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/267,570

(22) Filed: Jul. 13, 2025

(51) Int. Cl.
*A01H 5/02* (2018.01)

(52) U.S. Cl.
USPC ..... Plt./232

(58) Field of Classification Search
USPC ..... Plt./232
CPC ..... A01H 6/088; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new *Mandevilla* plant particularly distinguished by medium sized, bright red flowers, and medium compact upright growth habit, is disclosed.

1 Drawing Sheet

Genus and species: *Mandevilla sanderi.*
Variety denomination: 'KLEMS22083'.

BACKGROUND OF THE NEW PLANT

The present invention comprises a new and distinct variety of *Mandevilla*, botanically known as *Mandevilla sanderi*, and hereinafter referred to by the variety name 'KLEMS22083'. 'KLEMS22083' originated from a controlled cross-pollination conducted in December 2014 in Cobbitty, New South Wales, Australia between the proprietary female *Mandevilla* variety '13.21.1' (unpatented), and the proprietary male *Mandevilla* variety '13.21.5' (unpatented).

The seeds from the cross were sown and plants were grown for evaluation, where an individual plant designated 'KLEMS22083' was selected from the group of plants in Cobbitty, New South Wales, Australia in May 2016.

In March 2016, 'KLEMS22083' was first vegetatively propagated by vegetative cuttings in Cobbitty, New South Wales, Australia. 'KLEMS22083' was found to reproduce true to type in successive generations of asexual propagation via vegetative cuttings.

SUMMARY

The following are the most outstanding and distinguishing characteristics of this new variety when grown under normal horticultural practices in Cobbitty, New South Wales, Australia.

1. Medium bright red flowers, and
2. Medium compact upright growth habit

DESCRIPTION OF THE PHOTOGRAPH

This new *Mandevilla* plant is illustrated by the accompanying photograph which shows the plant's overall plant habit including form, buds, foliage, and flowers. The photograph is of a plant approximately 15-weeks-old grown indoors in Stuttgart, Germany in May 2023. The colors shown are as true as can be reasonably obtained by conventional photographic procedures.

DESCRIPTION OF THE NEW VARIETY

The following detailed descriptions set forth the distinctive characteristics of 'KLEMS22083'. The data which define these characteristics were collected from asexual reproductions carried out in Latina, Italy. Data was collected on sixteen-week-old plants grown in 2025. Color references are to The R.H.S. Colour Chart of The Royal Horticultural Society of London (R.H.S.), 5$^{th}$ edition (2007).

Classification:
- *Family.*—Apocynaceae.
- *Botanical.*—*Mandevilla sanderi.*
- *Common.*—*Mandevilla.*
- *Designation.*—'KLEMS22083'.

Parentage:
- *Female parent.*—'13.21.1' (unpatented).
- *Male parent.*—'13.21.5' (unpatented).

Propagation:
- *Type.*—Cuttings.
- *Time to produce a rooted young plant.*—8 weeks.
- *Root description.*—Ovate, limited rhizome production.
- *Rooting habit.*—Normal.

Plant description:
- *Plant and growth habit.*—Medium compact upright.
- *Plant height.*—40.0 cm.
- *Plant diameter.*—25.0 cm.
- *Number of climbing tendrils.*—None.

Lateral branch description:
- *Branching habit.*—Moderate.
- *Length.*—16.0 cm.
- *Diameter.*—0.4 cm.
- *Internode length.*—4.0 cm.
- *Strength.*—Strong.
- *Texture.*—Smooth.
- *Color.*—RHS 146A.

Foliage description:
*Arrangement*.—Opposite.
*Length*.—5.2 cm.
*Width*.—2.7 cm.
*Shape*.—Composed.
*Apex*.—Cuspidate.
*Base*.—Obtuse.
*Margin*.—Entire.
*Texture*.—Upper surface: Smooth. Lower surfaces: Smooth.
*Venation pattern*.—Pinnate.
*Color*.—Developing leaves: Upper surfaces: RHS 146A. Lower surfaces: RHS 146C. Fully expanded leaves: Upper surface: RHS 137B. Lower surface: RHS 144A.

Petioles:
*Length*.—0.9 cm.
*Diameter*.—0.1 cm.
*Texture*.—Upper surfaces: Smooth. Lower surfaces: Smooth.
*Color*.—Upper surface: RHS 141B and RHS 141C. Lower surface: RHS 139D.

Flower description:
*Flower type and habit*.—Single.
*Natural flowering season*.—Spring, summer, autumn.
*Flower longevity on the plant*.—10 days.
*Fragrance*.—Absent.

Flowers:
*Appearance*.—Glossy.
*Diameter*.—8.6 cm.
*Length*.—5.7 cm.
*Throat diameter*.—1.9 cm.
*Tube length*.—5.5 cm.
*Tube diameter, at the base*.—0.45 cm.

Flower buds:
*Height*.—8.2 cm.
*Diameter*.—1.5 cm.
*Shape*.—Tubular.
*Color*.—RHS 46A.

Corolla:
*Arrangement/appearance*.—Radial, glossy.
*Tube length*.—3.5 cm.
*Appearance*.—Radical.
*Petal lobe length*.—3.5 cm.
*Petal lobe width*.—3.5 cm.
*Petal lobe shape*.—Spatulate.
*Petal apex*.—Cuspidate.
*Petal margin*.—Entire.
*Petal texture*.—Upper surfaces: Smooth. Lower surfaces: Smooth. Throat texture: Slight ribbed. Tube texture: Slight ribbed. Color: Petal lobe: When opening: Upper surface: RHS 46A. Lower surface: RHS 46A. Fully opened: Upper surface: RHS 46B. Lower surface: RHS 46A. Throat: RHS 53A. Tube: RHS 35A.

Sepals:
*Arrangement/appearance*.—Single whorl.
*Length*.—1.1 cm.
*Width*.—2.2 cm.
*Shape*.—Lanceolate.
*Apex*.—Acuminate.
*Margin*.—Entire.
*Texture*.—Upper surface: Smooth. Lower surface: Smooth.
*Color*.—Inner surface: RHS 1B. Outer surface: RHS 14C.

Peduncles:
*Length*.—8.0 cm.
*Diameter*.—0.3 cm.
*Texture*.—Smooth.
*Strength*.—Strong.
*Aspect*.—About 45 degrees to axis.
*Color*.—RHS 146C.

Pedicels:
*Length*.—2.7 cm.
*Diameter*.—0.25 cm.
*Texture*.—Smooth.
*Strength*.—Strong.
*Aspect*.—About 45 degrees to axis.
*Color*.—RHS 180C.

Reproductive organs:
*Stamens*.—Quantity per flower: Five. Filament length: Less than 0.5 cm. Filament color: RHS 14B. Anther shape: Ellipsoidal. Anther size: 1.0 cm. Anther color: RHS 7C. Pollen amount: Medium. Pollen color: RHS 2D.
*Pistils*.—Quantity per flower: One. Pistil length: 3.0 cm. Stigma shape: Rounded. Stigma color: RHS 7C. Style length: 2.7 cm. Style color: RHS 7C. Ovary color: RHS144D.

Fruit and seed set: To date, fruit and seed development have not been observed on plants.

Disease and pest/insect resistance: No disease or pest resistance observed to date.

COMPARISON WITH PARENTAL LINES AND KNOWN VARIETY

'KLEMS22083' is distinguished from its parents as described in Table 1.

TABLE 1

Comparison with Parental Lines

| Trait | Variety 'KLEMS22083' | Female parent | Male Parent |
|---|---|---|---|
| Flower size | Medium | Medium large | Small |
| Flower color | Bright red | Dark red | Dark red |

'KLEMS22083' is most similar to the commercial *Mandevilla* variety 'Suntory Classic Red' (unpatented). Differences between the varieties are described in Table 2.

TABLE 2

Comparison with Similar Variety

| Trait | Variety 'KLEMS22083' | Commercial line 'Suntory Classic Red' |
|---|---|---|
| Flower fading | Slight fading in sun | Strong fading in sun |

I claim:

1. A new and distinct variety of *Mandevilla* plant designated 'KLEMS22083' as illustrated and described herein.

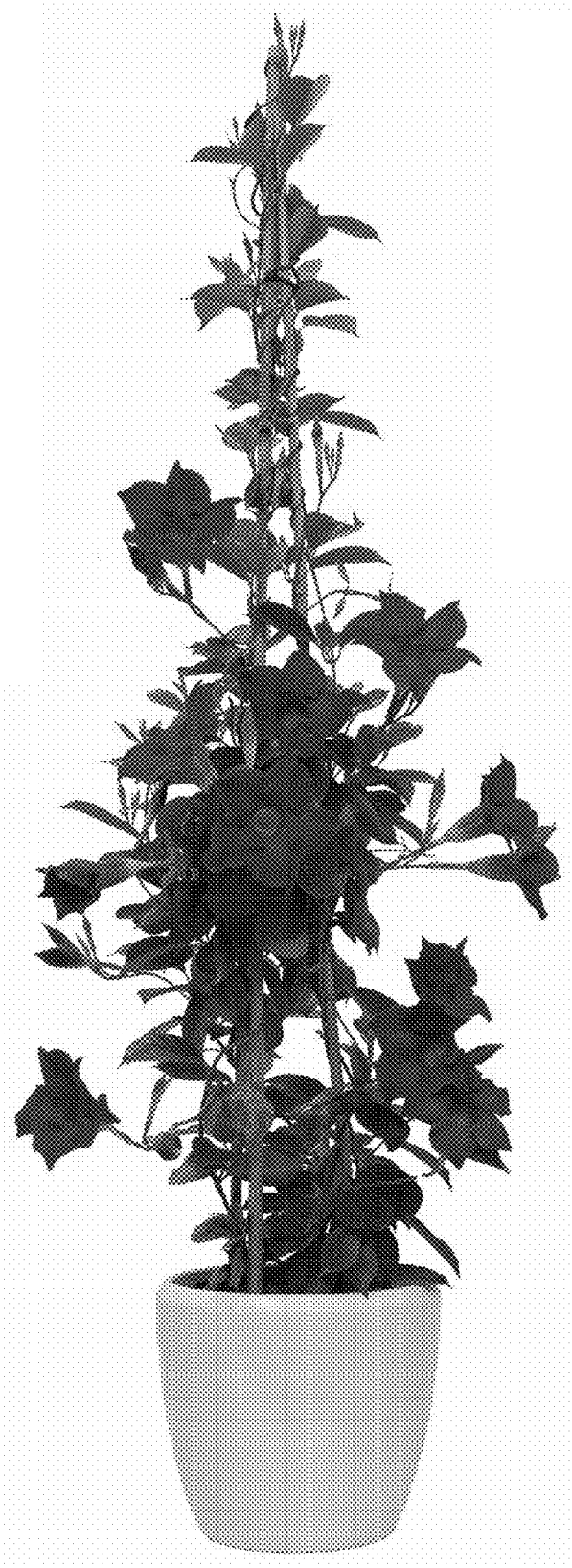

* * * * *